United States Patent [19]

Fujii et al.

[11] 4,297,486
[45] Oct. 27, 1981

[54] AMINOGLYCOSIDE ANTIBIOTIC G-367-1 AND METHOD FOR THE PRODUCTION THEREOF

[75] Inventors: Tadashiro Fujii, Mishima; Shuzo Satoi, Shizuoka; Naoki Muto, Shizuoka; Mitsuo Hayashi, Shizuoka; Akira Kodama, Shizuoka; Masaru Otani, Shizuoka, all of Japan

[73] Assignee: Toyo Jozo Kabushiki Kaisha, Shizuoka, Japan

[21] Appl. No.: 137,292

[22] Filed: Apr. 3, 1980

[30] Foreign Application Priority Data

Apr. 4, 1979 [JP] Japan .................................. 54-41274
Aug. 16, 1979 [JP] Japan ............................... 54-104770

[51] Int. Cl.³ .......................................... C07H 15/22
[52] U.S. Cl. .................. 536/17 R; 424/181; 435/80
[58] Field of Search ..................... 536/17 R

[56] References Cited

U.S. PATENT DOCUMENTS 3,997,524 12/1976 Nagabhushan ................... 536/17 R
4,002,742 1/1977 Wright et al. .................... 536/17 R
4,224,315 9/1980 Stadler et al. .................... 536/17 R

OTHER PUBLICATIONS

"The Merck Index", Nineth Ed., 1976, p. 8292, Merck & Co., Inc., Rahway, N.J., U.S.A.

Primary Examiner—Johnnie R. Brown
Attorney, Agent, or Firm—Young & Thompson

[57] ABSTRACT

Aminoglycoside antibiotic G-367-1 believed to have the formulae

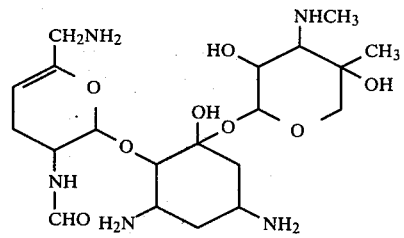

is produced by culturing Dactylosporangium thailandense G-367 FERM-P No. 4840 in a nutrient medium and separating the produced antibiotic therefrom. It has strong antibacterial effect against Gram negative bacteria.

1 Claim, 2 Drawing Figures

AMINOGLYCOSIDE ANTIBIOTIC G-367-1 AND METHOD FOR THE PRODUCTION THEREOF

This invention relates to novel aminoglycoside antibiotic G-367-1 and non-toxic salts thereof and a process for the production thereof.

The novel aminoglycoside antibiotic G-367-1 (hereinafter called G-367-1) has the following physicochemical properties.

m.p.: 130°–133° C.

$[\alpha]_D^{24}$: +188.9° (c=1.0, $H_2O$).

Elemental analysis: Found: C%=50.14, H%=7.60, N%=14.42: Calculated: C%=50.51, H%=7.84, N%=14.73.

Molecular weight: 475 (by mass spectrum).

Molecular formula: $C_{20}H_{37}N_5O_8$

Ultraviolet absorption spectrum: no characteristic maximum absorption peak at 220–360 nm, showing only end absorption.

Infrared absorption spectrum (KBr): shown in FIG. 1. absorption bands at 3350, 2920, 1660, 1590, 1380, 1140, 1100, 1050, 1000, 950 $cm^{-1}$.

NMR spectrum (hydrogen nucleus): shown in FIG. 2. ($D_2O$, 100 MHz, inner standard: DSS).

NMR spectrum (carbon nucleus: ($D_2O$, 25 MHz, inner standard: dioxane).

| No. | ppm | No. | ppm |
|---|---|---|---|
| 1 | 164.8 | 7 | 85.3 |
| 2 | 150.6 | 8 | 75.3 |
| 3 | 101.4 | 9 | 73.2 |
| 4 | 98.1 | 10 | 70.2 |
| 5 | 96.3 | 11 | 68.6 |
| 6 | 87.8 | 12 | 67.4 (dioxane) |
| 13 | 64.2 | 17 | 43.3 |
| 14 | 51.7 | 18 | 37.8 |
| 15 | 50.1 | 19 | 36.3 |
| 16 | 45.5 | 20 | 23.4 |
|  |  | 21 | 22.5 |

Solubility: soluble: water, methanol. insoluble: acetone, benzene, ethyl acetate, chloroform.

Color reaction: positive: ninhydrin, decolorization of potassium permanganate. negative: Elson-Morgan, Biuret.

Color: white powder.

Nature: basic.

Thin layer chromatography (silica-gel):

lower layer of chloroform:methanol:28% aq. ammonia (1:1:1), Rf=0.36

10% ammonium acetate:methanol (1:1), Rf=0.13

Referring to the above physico-chemical properties, G-367-1 is a novel aminoglycoside compound and its molecular structure is believed to be as follows:

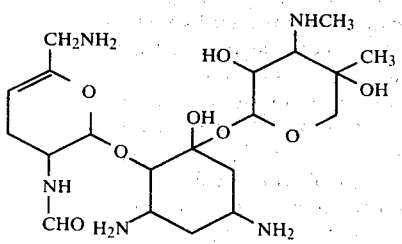

The antimicrobial spectrum (minimum inhibitory concentration, MIC) of G-367-1 by agar dilution method is as follows:

| Test organisms | MIC (mcg/ml) |
|---|---|
| Staphylococcus aureus ATCC 6538P | 6.3 |
| Staphylococcus aureus MS 27 | 6.3 |
| Staphylococcus aureus 0119 | 12.5 |
| Staphylococcus epidermidis sp-al-1 | 1.6 |
| Streptococcus pyogenes N.Y.5 | 6.3 |
| Bacillus subtilis ATCC 6633 | 0.8 |
| Escherichia coli NIHJ-JC2 | 1.6 |
| Escheria coli W3630 | 1.6 |
| Escheria coli W3630 RGN14 | 1.6 |
| Citrobacter freundii GN346 | 1.6 |
| Klebsiella pneunonia ATCC 10031 | 1.6 |
| Salmonella enteritidis Gartner | 1.6 |
| Shigella sonnei E33 | 1.6 |
| Proteus morganii 0239 | 3.1 |
| Proteus rettgeri ACR | 3.1 |
| Enterobacter aerogenes 0655 | 1.6 |
| Enterobacter cloacae GN366 | 1.6 |
| Serratia marcescens | 25 |
| Pseudomonas aeruginosa IAM1095 | 25 |
| Pseudomonas aeruginosa ML4561 | 25 |
| Pseudomonas aeruginosa ML4561 Rms166 | >100 |
| Pseudomonas aeruginosa ML4561 Rms164-1 | 50 |
| Pseudomonas aeruginosa ML4561 RP4 | 12.5 |
| Pseudomonas aeruginosa 1946 | >100 |
| Pseudomonas aeruginosa 2512 | >100 |
| Pseudomonas putida 1842 | >100 |
| Pseudomonas maltophilia 1850 | >100 |

The antibiotic G-367-1 of the present invention has strong antibacterial effect against Gram negative bacteria, and can be used as non-toxic acid addition salts of organic or inorganic acid such as the hydrochloride, hydrobromide, sulfate, phosphate, carbonate, acetate, fumarate, maleate, citrate, mandelate, succinate, ascorbate, aspartate or glutamate.

The antibiotic G-367-1 or non-toxic acid addition salts thereof may be used as injectable preparations, for example in the form of 20-40 mg vials or ampules.

The G-367-1 producing actinomycetes strain G-367 was isolated from a soil sample from a field in Fuji-shi, Shizuoka-ken, Japan, and is referred to as *Dactylosporangium thailandense* G-367. This strain was deposited in the Institute for Microbial Industry and Technology, Japan, as FERM-P No. 4840.

The taxonomical properties of the strain are as follows:

[I] Morphological properties

Observations on calcium-maleate agar [Bact. Rev., 21, 1 (1957)] at 30° C. for 3–7 days cultivation are as follows:

Substrate mycelium is curved or wavy, branched growth, non-fragmented, 0.5~0.8μ in diameter and no formation of aerial hyphae.

Globose or elliptical body of 1.5–2.0×2.0–2.5μ formed on the substrate mycelium embedded in the agar medium.

Short sporangiophores emerge from the substrate mycelium and finger-shaped sporangia are formed singly or in tufts on the surface of the agar medium. The size of the sporangia is 1.0–1.5×4.0–6.5μ. Each sporangium contains a vertical single row of three to four spores. The spores are motile in water, with globose, elliptical or pyriform shape, 1.0–1.5×1.5–2.5μ in size, by polytrichous polar flagella.

[II] Composition of diaminopimelic acid

Meso-type and lower Rm value than meso-type (slow moving diaminopimelic acid) by whole mycelial analysis were detected.

[III] Growth on various media

Observations on various media at 30° C. for 14 days are illustrated in the following table. Aerial mycelium is not formed except on oatmeal agar in a rudimentary form. Formation of sporangia is good on calcium maleate agar, moderate on soil agar [J. Gen. Microbiol., 50, 295 (1968)], and slight or no formation on the other media.

Color indication is based on "Color Harmony Manual", 4th Ed. 1958 (Container Corporation of America).

| Growth on various media | | | |
|---|---|---|---|
| Medium | Growth | Color of substrate mycelium | Soluble pigment |
| Sucrose-nitrate agar (Waksmann medium No. 1)* | moderate to poor | Apricot (4ia) to Dusty Orange (4lc) | none |
| Glucose-asparagine agar (Waksmann medium No. 2)* | poor | Brite Melon Yellow (4ia) (3ia) to Apricot | " |
| Glycerin-asparagin agar (ISP medium No. 5)** | little to poor | Light Melon colorless to Yellow (3ea) | " |
| Starch-inorganic agar (ISP medium No.4)** | moderate to good | Russet Orange (4nc) to Dusty orange (4lc) | " |
| Tyrosine agar (ISP medium No. 7)** | little to poor | Apricot (4ga) to Pale Pastel Orange (4ic) | " |
| Oat meal agar (ISP medium No. 3)** | moderate to good | Orange Rust (4pe) to Russet Orange (4pc) | " |
| Yeast extract-malt extract agar (ISP medium No. 2)** | " | Maple (4le) to Luggage Tan (4ne) | Maple (4le) to Light Brown (4ng) |
| Calcium-malate agar | poor | colorless | none |
| Nutrient agar (Waksmann medium No. 14)* | little | " | " |
| Benett agar (Waksmann medium No. 30)* | moderate to good | Maple (4le) to Luggage Tan (4ne) | Maple (4le) to Light Brown (4ng) |
| Emerson agar (Waksmann medium No.28)* | moderate | Pastel Orange (4ic) to Maple (4le) | Maple (4le) |
| Hickey and Tresner agar (Waksmann medium No. 32)* | moderate to good | Cinnamon (3le) to Maple (4le) | Maple (4le) to Light Spice Brown (4lg) |
| Glucose-yeast extract agar (Waksmann medium No. 29)* | moderate | Melon Yellow (3ga) | none |
| Peptone-yeast extract-iron agar (IPS medium No.6)** | little | colorless | " |
| Soil agar | little to poor | " | " |
| Potato stabb (Waksmann medium No. 40)* | moderate | Tile Red (5ne) to Copper (5lc) | " |
| Potato stabb + calcium carbonate | " | Tile Red (5ne) to Copper (5lc) | " |
| Carrot stabb | little | colorless | " |

*Waksmann S.A. 'The Actinomycetes' Vo/2 1961 P.327-334 Williams & Wilkins co.
**Inter. J. Syst. Bact. 16:313~340(1966)
***Antimicrob. Agents and Chemother. 1963 P. 116~124

(1) Utilization of carbon sources:

| Carbon source | P & G* | Lm* |
|---|---|---|
| D-arabinose | ± | + |
| L-arabinose | + | + |
| D-fructose | + | + |
| D-galactose | + | + |
| D-glucose | + | + |
| glycerol | − | − |
| i-inositol | − | − |
| D-mannose | + | + |
| D-mannitol | + | + |
| α—melibiose | + | + |
| β-lactose | + | ± |
| dulcitol | − | − |
| D-trehalose | + | + |
| D-cellobiose | + | + |
| melezitose | + | + |
| raffinose | + | − |
| L-rhamnose | + | + |
| D-ribose | − | − |
| L-sorbose | − | − |
| D-sorbitol | − | − |
| sucrose | + | + |
| D-xylose | + | + |
| adonitol | − | − |
| salicin | ±~+ | ±~+ |
| starch | + | + |
| maltose | + | + |
| dextrin | + | + |
| inulin | − | − |

+: positive
±: weakly positive
−: negative
*Pridham-Gotlieb inorganic medium
**Inter. J. Syst. Bact., 21, 240-247 (1971)

(2) Growth temperature: 20°-40° C.
(3) Peptonization and coagulation of skim milk: positive
(4) Formation of melanin-like pigment: negative on tyrosine and peptone-yeast extract-iron agar.
(5) Starch hydrolysis: positive
(6) Cellulose decomposition: negative
(7) Caseine decomposition: positive
(8) Tyrosine decomposition: negative
(9) Gelatin liquefaction: positive
(10) $H_2S$ formation: weakly positive
(11) Nitrate reduction: positive
(12) Growth pH: pH 5.5-9.0

As hereinabove illustrated, the characteristics of strain G-367 are finger-shaped sporangia grown on substrate mycelium, a vertical single row of spores in sporangium, and polytrichous polar flagellae on spores.

Thus, the sporangia form and the polytrichous flagella belong to the genus Actinoplanaceae, and more particularly, the finger-shaped sporangia and the vertical single row of spores belongs to the genus Dactylosporangium.

Furthermore, as the strain G-367 shows orange-brown to brown color substrate mycelium and a brown soluble pigment, the strain is referred to as *Dactylosporangium thailandense* [Arch. Microbiol., 58, 42–52 (1967)]. Therefore the strain is designated as *Dactylosporangium thailandense* G-367.

The production of the novel antibiotic G-367-1 can be carried out by aerobically cultivating a G-367-1 producing strain belonging to the genus Dactylosporangium in a conventional medium. Solid or liquid media can be used; and for large scale production, a liquid medium is preferable.

Conventional nutrient media for microorganisms can be used. Assimilable carbon sources such as glucose, sucrose, maltose, starch, dextrin and molasses can be used. Assimilable nitrogen sources such as corn steep liquor, soybean powder, cotton seed powder, wheat gluten, peptone, meat extract, yeast extract, caseine hydrolyzate, ammonium salt and nitrate can be used. Phosphates and salts of magnesium, calcium, potassium, sodium, cobalt, iron (++) or manganese can be used if desired.

Cultivation temperature depends on the growth of the microorganisms and production of antibiotic and is preferable at 25°–35° C. Cultivation time depends on the conditions and is usually 100–200 hours. Cultivation is terminated at the maximum potency of the antibiotic in the medium.

The antibiotic is produced in the culture filtrate.

Isolation of G-367-1 can be effected by conventional isolation methods for water-soluble basic aminosugar antibiotics.

G-367-1 can be assayed on agar plate using *Bacillus subtilis* as test organisms.

Examples of isolation and purification methods for G-367-1 are as follows:

Culture filtrate is obtained by adjusting the cultured medium to acidic pH and neutralizing and then filtering the same. The cultured filtrate is charged on a column of cation exchange resin such as Amberlite IRC-50 ($NH_4^+$ type) to adsorb active substances, and the active substances are eluted with 2 N-aqueous ammonia and concentrated and the pH of the eluate is adjusted. The concentrate is charged on a column of cation exchange resin such as CM-Sephadex C-25 ($NH_4^+$ type), eluted with aqueous ammonia of 0–0.35 N concentration gradient to obtain the active fractions which are concentrated and lyophilized to obtain G-367-1 as a purified white powder, in the form of the free base. The thus-obtained G-367-1 shows a single spot upon thin layer chromatography.

The following examples illustrate embodiments of the present invention but are not to be construed as limiting:

EXAMPLE 1

Medium (pH 7.0, 100 ml) containing dextrin 1%, glucose 1%, casein hydrolyzate 0.5%, yeast extract 0.5% and calcium carbonate 0.1% in a 500 ml-Erlenmeyer flask was sterilized at 120° C. for 20 minutes.

One loopful *Dactylosporangium thailandense* G-367 of agar slant medium was inoculated and shake cultured at 30° C. for 120 hours. This seed culture was inoculated into the sterilized medium of the same composition (20 l.) in a 30 l. jar-fermenter and cultured at 30° C. for 72 hours at 300 r.p.m., with 20 l./min aeration. The said cultured medium (10 l.) was inoculated into a sterilized medium containing dextrin 5%, glucose 0.5%, defatted soybean powder 3%, calcium carbonate 0.7% and cobalt chloride 1.3 ppm (pH 7.2, 200 l.) in a 250 l.-tank and cultured at 30° C. for 120 hours, at 250 r.p.m. with aeration of 100 l./min to obtain 190 l. of cultured medium.

EXAMPLE 2

Cultured medium obtained in Example 1 was adjusted to pH 2 by adding 12 N sulfuric acid, stirred for 30 minutes, further adjusted to pH 7.0 by adding conc. aqueous ammonia and filtered after addition of filter-aid "Perlite" (tradename) (4 kg). The filtrate was charged on a column of Amberlite IRC-50 (Rohm and Haas Co.) ($NH_4^+$ type, 10 l.), and eluted with 2 N aqueous ammonia (20 l.) after washing with water. The eluate was concentrated in vacuo up to 100 ml volume.

The concentrate was adjusted to pH 7.0 by adding 6 N sulfuric acid and charged on a column of CM-Sephadex G-25 (Pharmacia Fine Chem. Co.) ($NH_4^+$ type, 500 ml, diameter 4 cm). After washing with water, the active substances were eluted by gradient elution with aqueous ammonia (5 l.) of 0–0.35 N concentration gradient. Each fraction was checked by thin layer chromatography using a lower layer of chloroform:methanol:28% aqueous ammonia (1:1:1) and the active substance was confirmed by ninhydrin coloring. G-367-1 was found in fractions Nos. 175–185. The active fractions were combined, concentrated in vacuo, and freeze dried to obtain a white powder. The powder was dried at 40° C. for 48 hours over phosphorus pentoxide under reduced pressure to yield purified G-367-1 as a white powder (free base, 750 mg).

Figure 1:
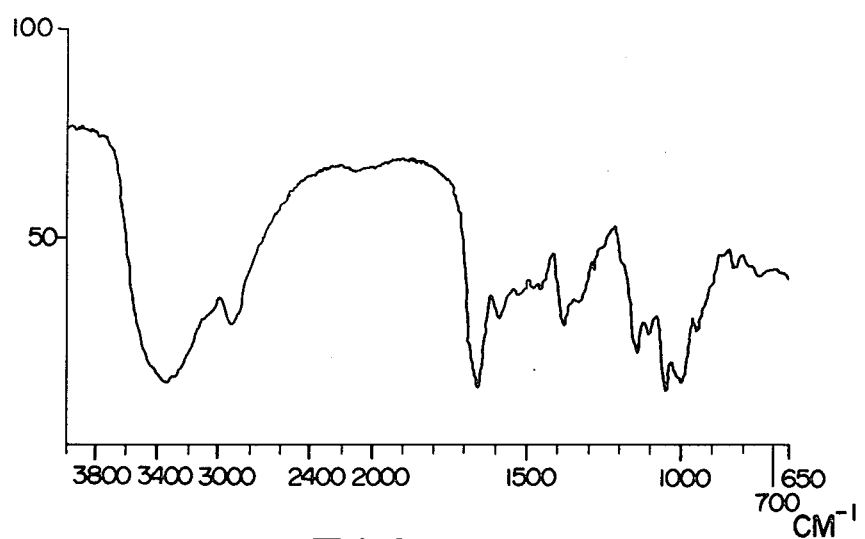
FIG. 1 is the IR spectrum of G-367-1.
Figure 2:
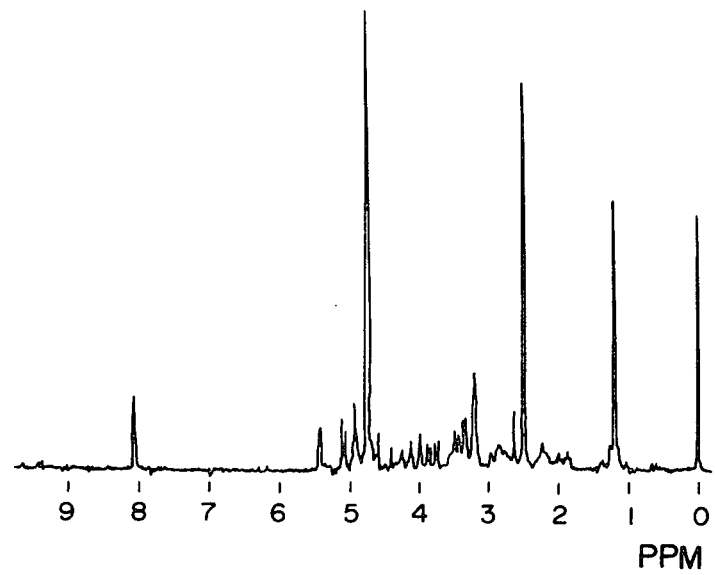
FIG. 2 is the NMR spectrum (hydrogen nucleus) of G-367-1.

What is claimed is:

1. Aminoglycoside antibiotic of the formula

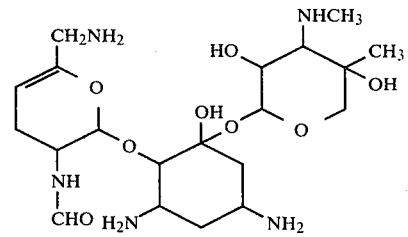

and the non-toxic acid addition salts thereof.

* * * * *